United States Patent
Smith

(10) Patent No.: US 9,974,804 B1
(45) Date of Patent: May 22, 2018

(54) STRONTIUM-BASED COMPOSITION, PRODUCT, AND METHOD OF USING THE SAME TO CONTROL PROGRESSION OF OSTEOARTHRITIS OSTEOPOROSIS AND TOOTH DECAY

(71) Applicant: David Lloyd Smith, West Linn, OR (US)

(72) Inventor: David Lloyd Smith, West Linn, OR (US)

( * ) Notice: Subject to any disclaimer, the term of this patent is extended or adjusted under 35 U.S.C. 154(b) by 0 days. days.

(21) Appl. No.: 15/699,422

(22) Filed: Sep. 8, 2017

(51) Int. Cl.
| | |
|---|---|
| A61K 9/68 | (2006.01) |
| A61K 33/00 | (2006.01) |
| A61K 31/194 | (2006.01) |
| A61K 31/375 | (2006.01) |
| A61K 31/519 | (2006.01) |
| A61K 31/593 | (2006.01) |
| A61K 9/20 | (2006.01) |
| A61K 9/00 | (2006.01) |
| A61Q 11/00 | (2006.01) |
| A61K 8/19 | (2006.01) |
| A61K 8/365 | (2006.01) |
| A61K 8/67 | (2006.01) |

(52) U.S. Cl.
CPC .......... *A61K 33/00* (2013.01); *A61K 8/19* (2013.01); *A61K 8/365* (2013.01); *A61K 8/67* (2013.01); *A61K 8/673* (2013.01); *A61K 8/676* (2013.01); *A61K 9/006* (2013.01); *A61K 9/0056* (2013.01); *A61K 9/0058* (2013.01); *A61K 9/20* (2013.01); *A61K 31/194* (2013.01); *A61K 31/375* (2013.01); *A61K 31/519* (2013.01); *A61K 31/593* (2013.01); *A61Q 11/00* (2013.01)

(58) Field of Classification Search
CPC .... A61K 2300/00; A61K 36/15; A61K 36/16; A61K 36/45; A61K 36/48; A61K 36/484; A61K 36/82; A61K 36/87; A61K 36/9068; A61K 45/06; A61K 31/167; A61K 47/32; A61K 31/192; A61K 31/4166; A61K 31/55; A61K 31/616; A61K 47/10; A61K 47/38; A61K 9/0004; A61K 9/0031; A61K 9/10; A61K 9/145; A61K 9/1617; A61K 9/1638; A61K 9/1652; A61K 9/2077; A61K 9/209; C09C 51/412; C09C 51/43; C09C 53/06; C09C 53/10; C09C 57/30; C09C 61/135; C09C 233/25; C09C 223/26; C09C 223/74; C09C 495/04
See application file for complete search history.

(56) References Cited

U.S. PATENT DOCUMENTS

| | | |
|---|---|---|
| 2003/0003059 A1 | 1/2003 | Dana |
| 2008/0193531 A1* | 8/2008 | Hermelin ............. A61K 9/2013 424/474 |
| 2013/0039865 A1 | 2/2013 | Truitt, III et al. |
| 2016/0198750 A1 | 7/2016 | Carlson et al. |

FOREIGN PATENT DOCUMENTS

| | | |
|---|---|---|
| CN | 101309602 A | 11/2008 |
| WO | 2013133903 A1 | 9/2013 |
| WO | 2016034942 A1 | 3/2016 |

OTHER PUBLICATIONS

Goldie, Maria Perno, "Potassium nitrate, sodium fluoride, strontium chloride, and NovaMin technologies for dentin hypersensitivity," Mar. 15, 2011, http://www.dentistryiq.com/articles/2011/03/novamin-and-hypersensitivity.html.

supplementclinic.com, "OsteoForte by Pure Horizon—3 Jar Pack—210 grams," http://www.supplementclinic.com/OsteoForte_by_Pure_Horizon_p/10240291-3.htm.

* cited by examiner

*Primary Examiner* — Nannette Holloman
(74) *Attorney, Agent, or Firm* — Brian Chew

(57) ABSTRACT

A strontium-based composition for controlling progression of osteoarthritis, osteoporosis, and tooth decay is presented. The composition may include a blend of ingredients including: at least 500 mg of strontium carbonate; citric acid; ascorbic acid; malic acid; folic acid; vitamin d3; magnesium citrate; natural sweetener; and flavoring. The all-natural strontium-based blend of ingredients is simply delivered to the oral cavity where an "in-vivo" chemical reaction takes place resulting in direct tooth and dentin exposure to facilitate direct dental anti-caries and anti-sensitivity strontium benefits. The blend of ingredients is then swallowed to establish intestinal transit and absorption to obtain the targeted benefits of systemic absorption to bone and joint areas.

14 Claims, No Drawings

STRONTIUM-BASED COMPOSITION, PRODUCT, AND METHOD OF USING THE SAME TO CONTROL PROGRESSION OF OSTEOARTHRITIS OSTEOPOROSIS AND TOOTH DECAY

BACKGROUND OF THE INVENTION

1. Field of Invention

The present invention relates generally to the field of health. More particularly, the present invention relates to the use of a natural, strontium-based blend of ingredients to control the progression of osteoarthritis, osteoporosis, and tooth decay.

2. Description of Related Art

Osteoarthritis is the most common worldwide joint condition with symptomatic disease affecting up to 20% of individuals aged over 50 years. Moreover, the socioeconomic burden is immense, costing society hundreds of billions of dollars a year. The etiology of osteoarthritis is multi-factorial and may be due in part to gravitation effects on weight-bearing joints and result from repetitive, life-long, joint specific minor or more defined major injuries. Osteoarthritis frequently affects axial areas such as the neck or low back joints as well as appendicular small hand joints and weight-bearing joints such as the hip or knee or foot. Obesity appears to play a role at least in the progression of symptomatic osteoarthritis in weight-bearing joints by excessive loading on the involved joint.

Medical treatment of osteoarthritis is limited to pain and anti-inflammation medication usage coupled with joint specific targeted steroid or hyaluronic acid derivative injection therapy. Surgical joint replacement has improved and in general is reserved for end-stage symptomatic disease in individuals who are otherwise in good health and have exhausted nonsurgical alternatives. More recently, medical treatment emphasis has shifted to earlier diagnosis (via magnetic resonance imaging) and earlier pharmaceutical intervention. Despite this important insightful change, no pharmaceutical agent is currently available that can (1) treat pain while (2) preventing or slowing down disease progression.

From a biomechanical and microscopic viewpoint, osteoarthritis is characterized as a dynamic process of ongoing hyaline or fibrocartilage cartilage (e.g. knee meniscus) deterioration coupled with progressive adaptive subchondral bone remodeling. There is increasing evidence that this is indeed a coupled metabolic interaction between bone cells such as osteoblasts, osteocytes and osteoclasts and cartilage cells such as apoptotic (dying) chondrocytes and chondroblasts that is regulated in part by surrounding intercellular chemical signal and inflammatory factors. The key is that clinically this interplay results is painful joint dysfunction. The coupling of bone and cartilage turnover and ongoing cartilage degeneration has sparked interest in employing bone antiresorptive and anabolic agents as therapeutic drugs. Several investigations have shown a positive effect on cartilage when bone resorption is suppressed or progression of cartilage degradation when bone resorption is increased.

From a practical point of view, osteoporosis is best characterized by decreased bone mass coupled with increased risk of low impact fracture. The risk of osteoporosis increases with age. Worldwide, approximately 15% of the elderly (both men and women) are affected by this weakened bone condition which results in almost 9 million bone fractures (e.g., wrist, rib, vertebral, hip) every year. The mechanism of osteoporosis is a dysregulation of bone resorption and bone formation during ongoing bone remodeling. A combination of inadequate bone mass coupled with excessive bone resorption and suboptimal new bone formation during remodeling results in fragile bone tissue. An interplay of hormone deficiency (e.g., estrogen or testosterone), decreased vitamin d and deficiency of calcium can lead to increased bone resorption and poor new bone formation. At a cellular level, dysregulation of bone building osteoblasts and bone resorbing osteoclasts influenced by other extracellular inflammatory mediators play a significant role and underlie the development and progression of osteoporosis. Certain medications such as long-term use of glucocorticoids, anti-seizure medications, anticoagulants and proton pump inhibitors have a been linked to both the development or worsening of osteoporosis.

Treatment and prevention of osteoporotic weakened bone are aimed at maintaining adequate or restoring essential calcium and vitamin D bone stores. Usually, oral supplementation of these nutrients is coupled with weight bearing and muscle strengthening exercise. In addition, lifestyle changes that help include cessation of cigarette smoking and alcohol use. Pharmaceutical medications such as bisphosphonates or other anti-osteoporotic drugs such as denosumab which increase bone mineral density can also be employed. Bisphosphonates inhibit osteoclastic bone resorption by attaching to binding sites on bony surfaces while denosumab inhibits this maturation of osteoclasts. Direct stimulation of bone formation with parathyroid hormone related anabolic agents can also be employed. Use of these prescription medications are limited by cost, side effects and patient preference. Severe bisphosphonate adverse effects include bisphosphonate-related osteonecrosis of the jaw and atypical femur bone fractures. In the elderly, this can result in the loss of teeth, inability to undergo dental implant surgery and femur fracture repair.

Dental caries (tooth decay) remains a world-wide endemic problem and is the most common endemic dental issue in many populations. Dietary overuse of refined sugars such as sucrose are a well-established contributor to the increased rate of dental caries in developed societies. Tooth decay results from ongoing tooth surface caries formation over time. Ongoing deepening tooth decay frequently results in periodontal tooth infection and pain ultimately coupled with chewing failure and tooth loss. The tooth cavity starts at the tooth surface which consists of enamel or dentin. The involved tooth becomes surrounded by caries-causing bacteria which ferment carbohydrates such as sucrose or fructose. As part of this fermentation process, acids such as lactic acid are produced and accumulate around portions of tooth structure. In a susceptible host, these acids will cause tooth demineralization if left unchecked by the natural wetting, diluting and neutralizing action of saliva.

Oral use of xylitol, a natural sugar alcohol sweetener either in chewing gum or lozenge form, helps to prevent caries development since it is not fermentable in the oral cavity. In addition, xylitol can carry polyvalent cations like calcium or strontium into an arranged xylitol ligand for transport and presentation to the gut wall mucosa for improved systemic absorption. Possibly, this can help remineralize deeper enamel before further caries progression can develop. Fluoride containing toothpastes, although unnatural, are helpful by decreasing demineralization, in part by binding to the hydroxyapatite crystals in enamel.

Osteoarthritis, osteoporosis, and dental caries are not conditions that overlap in medical or scientific disciplines. For example, rheumatologists that specialize in joint conditions, orthopedists that specialize in bone and joint surgery, endocrinologists who specialize in bone metabolism disorders, and doctors of medical dentistry (DMDs) do not typically read one another's specific scientific research. As a result, there lacks a medical or scientific solution that mutually addresses these various conditions.

Based on the foregoing, there is a need in the art for a single solution that can control progression of and medically treat the three distinct disorders of osteoarthritis, osteoporosis, and dental caries (tooth decay).

The above problems in the related art are considered as matters that have been addressed by the inventor to derive the present inventive concept, or as matters discovered during the course of deriving the present inventive concept. Thus, the problems may not be simply referred to as information that was known to the general public prior to filing the present disclosure.

SUMMARY OF THE INVENTION

One or more exemplary embodiments of the present invention include a strontium-based composition for controlling progression of osteoarthritis, osteoporosis, and tooth decay. The composition may include a blend of ingredients including: at least 500 mg of strontium carbonate; citric acid; ascorbic acid; malic acid; folic acid; vitamin d3; magnesium citrate; natural sweetener; and flavoring.

In another exemplary embodiment, each rounded ¼-⅜ tsp of the blend of ingredients may include: 500-1500 mg of strontium carbonate; 50-150 mg of citric acid; 50-150 mg of ascorbic acid; 50-150 mg of malic acid; 0.5-2 mg of folic acid; 2-7 mcg of vitamin d3; 50-100 mg of magnesium citrate; 105-1015 mg of natural sweetener; and 10-60 mg of flavoring.

In another exemplary embodiment, each rounded ¼-⅜ tsp of the blend of ingredients may include: 800-1200 mg of strontium carbonate; 50-75 mg of citric acid; 50-75 mg of ascorbic acid; 50-75 mg of malic acid; 0.75-1.5 mg of folic acid; 2-5 mcg of vitamin d3; 50-75 mg of magnesium citrate; 510-1015 mg of natural sweetener; and 30-50 mg of flavoring.

In another exemplary embodiment, the 510-1015 mg of natural sweetener may include 5-15 mg of stevia and 100-1000 mg of xylitol.

In another exemplary embodiment, the composition may include one rounded ¼-⅜tsp of the blend of ingredients mixed with 2 oz of water.

In another exemplary embodiment, the natural sweetener may be at least one of stevia and xylitol.

In another exemplary embodiment, the blend of ingredients may include only natural compounds.

One or more other exemplary embodiments of the present invention include a strontium-based product for controlling progression of osteoarthritis, osteoporosis, and tooth decay. The product may include a blend of ingredients including: 500-1500 mg of strontium carbonate; 50-150 mg of citric acid; 50-150 mg of ascorbic acid; 50-150 mg of malic acid; 0.5-2 mg of folic acid; 2-7 mcg of vitamin d3; 50-100 mg of magnesium citrate; 105-1015 mg of natural sweetener; and 10-60 mg of flavoring; and a carrier combined with the blend of ingredients In an exemplary embodiment, the carrier may be an ingredient-enriched soft tablet.

In another exemplary embodiment, the carrier may be an ingredient-enriched dissolvable tablet.

In another exemplary embodiment, the carrier may be an ingredient-enriched lozenge.

In another exemplary embodiment, the carrier may be a toothpaste.

In another exemplary embodiment, the carrier may be a piece of chewing gum.

In another exemplary embodiment, the carrier may be an oral spray.

One or more other embodiments of the present invention may include a method of delivering a strontium-based composition for controlling progression of osteoarthritis, osteoporosis, and tooth decay. The composition may include one rounded ¼-⅜ tsp of a blend of ingredients in a dry powder form, the blend of ingredients comprising 500-1500 mg of strontium carbonate, 50-150 mg of citric acid, 50-150 mg of ascorbic acid, 50-150 mg of malic acid, 0.5-2 mg of folic acid, 2-7 mcg of vitamin d3, 50-100 mg of magnesium citrate, and 105-1015 mg of natural sweetener; and 10-60 mg of flavoring. The method may include: mixing the blend of ingredients with 2 oz. of water to form a slurry; swishing the slurry in an oral cavity; and swallowing the slurry after the swishing.

The foregoing, and other features and advantages of the invention, will be apparent from the following, more particular description of the exemplary and preferred embodiments of the invention, the accompanying drawings, and the claims.

DETAILED DESCRIPTION OF PREFERRED EMBODIMENTS

Embodiments of the invention are discussed below with reference to the Figures. However, those skilled in the art will readily appreciate that the detailed description given herein with respect to these figures is for explanatory purposes as the invention extends beyond these limited, exemplary embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following exemplary embodiments described and shown. That is, there are numerous modifications and variations of the invention that are too numerous to be listed but that all fit within the scope of the invention.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

From reading the present disclosure, other variations and modifications will be apparent to persons skilled in the art. Such variations and modifications may involve equivalent and other features which are already known in the art, and which may be used instead of or in addition to features already described herein.

Although claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any claim and whether or not it mitigates any or all of the same technical problems as does the present invention.

Features that are described in the context of separate embodiments may also be provided in combination in a single embodiment. Conversely, various features that are, for brevity, described in the context of a single embodiment, may also be provided separately or in any suitable subcombination. New Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art, many careful considerations and compromises typically must be made when designing for the optimal manufacture of a commercial implementation any system, and in particular, the exemplary embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

As will be understood by one skilled in the art, all ranges recited herein also encompass any and all possible sub-ranges and combinations of sub-ranges thereof, as well as the individual values making up the range, particularly integer values. Any listed range can be easily recognized as sufficiently describing and enabling the same range being broken down into at least equal halves, thirds, quarters, fifths, or tenths. A recited range (e.g., weight percent, absolute weight) includes each specific value, integer, decimal, or identity within the range. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specified values recited for radicals, substituents, and ranges, are for illustration only; they do not exclude other defined values or other values within defined ranges for radicals and substituents.

The present invention will now be described in detail with reference to exemplary embodiments thereof Strontium is a widely available earth alkaline metal and exists most commonly in nature in two forms: $SrSO_4$ (strontium sulfate) and $SrCO_3$ (strontium carbonate). It is a nonessential element in human and other mammalian biologic processes, and it is present in drinking water and soil in a few milligrams (mg) per liter. Strontium is therefore naturally present in low concentrations in the mammalian body, mostly derived from dietary plant sources. The daily human intake of strontium (Sr) is about 2 mg per day, while calcium (Ca) is 1000 mg per day. This ratio is also reflected in the human body; the ratio between strontium and calcium (Sr:Ca) is about 2-3:1000. When supplemented in the human diet, natural stable strontium compounds such as strontium carbonate are well tolerated without reported toxicity. However, strontium in its natural water insoluble carbonate compound form is considered less absorbable from the small bowel, but when assimilated the majority is absorbed from the jejunum aspect of the small bowel.

in humans, there is preferential calcium absorption over strontium in the small bowel. Supplementation with strontium compounds such as strontium lactate or gluconate can increase serum strontium levels several folds such that the serum level varies mostly on the length of supplementation. Dietary nutrients such as vitamin d, the solubility of strontium salt used, and the spacing of strontium intake from daily calcium ingestion can also influence serum strontium levels since calcium and strontium ions share small bowel binding absorption sites. Strontium and calcium share excretion pathways in the renal tubule; the daily renal clearance of strontium is about three times that of calcium. Strontium has a predilection for bone; therefore, dietary strontium supplementation can be viewed as a naturally bone seeking element. Once oral cavity delivery and intestinal absorption is completed and serum levels are consistently generated, it is preferentially deposited in bone matrix or apatite. Oral daily supplementation with strontium compounds providing about 700 mg of the strontium cation do not effect serum calcium concentrations and in general for ever 10-20 calcium bone lattice crystals less than one is substituted with strontium. Once strontium supplementation is discontinued, bound strontium in bone matrix is gradually released and replaced again by calcium ions. Fifty percent of bone strontium disappears after 10 weeks.

Strontium containing compounds have been proposed as agents that restore both bone and cartilage biomechanical properties or at least demonstrate improvement in stanching progression of osteoarthritis. In vivo animal studies support this view; strontium compounds improve bone morphology while ameliorating early osteoarthritis cartilage degradation. In addition, in a clinical three-year human knee osteoarthritis study, daily oral strontium use resulted in meaningful statistically significant osteoarthritis related subjective pain decrease and objective decrease in joint space loss. Although the precise mechanism for this improvement is not known, evidence supports a dual targeting process in which bone abnormal subchondral bone remodeling is slowed while chondrocyte dysfunction is potentially halted.

An unnatural, synthesized strontium compound called strontium ranelate (ranelate is a manmade complex metal chelating organic acid) in previous reports has been shown to be an effective anti-osteoporotic drug by both its anti-resorptive and increased bone forming effects. However, study reported side effects although uncommon have limited its overall usefulness despite previous marketing and use in many countries other than the United States.

Naturally occurring strontium compounds such as strontium carbonate have been used for osteoporosis in the over-the-counter milieu because they lack known serious side effects and are well tolerated although anti-osteoporotic and dose effect has not been formally investigated. Strontium salts such as citrate, gluconate, and lactate have also been marketed as over the counter bone strengthening agents. No formal studies to date have been undertaken to address differences in effectiveness of these products compared to strontium ranelate. Strontium citrate, lactate, gluconate, and chloride are more water-soluble than strontium carbonate and produce substantial serum and bone tissue levels. No known side effects have been reported with these natural products despite many years of use compared to the ranelate product. A small osteoporosis Mayo clinic study in the 1950s pointed to an 84% marked subjective improvement with daily doses of 6.4 grams of strontium lactate for months to years. Furthermore, cessation of distribution of the ranelate product occurred in August of 2017 due to market conditions.

The bone in strontium ranelate treated individuals exhibited both trabecular and cortical bone thickness (14-18%) compared to placebo group and about a 10% increase in osteoblast activity parameters. From a biologic standpoint, strontium salts including chloride, citrate, and gluconate have all been shown to enter bone tissue with presumably the same bone building mechanism of action.

From a clinical standpoint, in elderly post-menopausal osteoporotic female patients, three-year daily use of strontium ranelate resulted in about a 49% reduction in vertebral fracture, 19% reduction in nonvertebral fracture and 36% in hip fracture when compared to the control group. Similar findings have been reported in men with osteoporosis. A suggested mechanism of bone strengthening is direct inhibition of osteoclast maturation and activation coupled with stimulation of osteoblast proliferation.

A natural way of decreasing tooth (dentin) sensitivity and stanching progression of tooth caries development is using strontium containing compounds. Several strontium containing varieties of toothpastes (strontium acetate) have been employed to reduce dentin hypersensitivity by blocking dentin tubules and protein precipitation. Evidence in many studies also points to the cariostatic effect of strontium itself or in the presence with fluoride. When used, strontium compounds have been shown to be present in saliva and dental plaque and to be topically adsorbed by both enamel and dentin and incorporated into the tooth crystal lattice. Besides direct tooth surface adsorption upon oral ingestion, strontium can be systemically incorporated into tooth lattice mineral and has been found to support remineralization of caries lesions. Overall, strontium compounds appear to support the tooth's ability to resist dissolution by occluding dentin tubules and incorporation into tooth structure lattice hydroxyapatite. In addition, formation of tooth surface strontium complexes may also resist bacterial cariogenic attacks.

Therefore, one or more exemplary embodiments of the present invention are directed to a composition including a natural blend of ingredients that can control the progression of osteoarthritis and reduce pain and stiffness if adhered to and compliantly used on a continued daily basis as directed, and may also help allay tooth sensitivity and decay (caries) as well as contain progression of osteoporosis (bone softening). In an exemplary embodiment, the blend of ingredients comprises strontium carbonate as an active ingredient, citric acid, ascorbic acid, malic acid, folic acid, vitamin d3, magnesium citrate, natural sweetener (e.g., stevia, xylitol), and desired flavorings. In a preferred embodiment, the blend of ingredients comprises only natural compounds.

In an exemplary embodiment, the composition is to be taken orally whereby an "in-vivo" chemical reaction occurs in the oral cavity. Particularly, the insoluble strontium carbonate combines with citric, ascorbic and malic acid in the oral cavity, resulting in strontium citrate, strontium ascorbate, strontium malate, carbon dioxide and water. These newly formed strontium salts are then more soluble for direct tooth surface enamel contact and potentiate adsorption. Upon intestinal transit, the newly formed, soluble strontium salts improve intestinal absorption by way of increasing luminal solubility when combined in ligand xylitol form while in luminal contact with vitamin d and magnesium. Due to the bone seeking innate character of strontium, the strontium citrate, strontium ascorbate and strontium malate delivered at higher levels to bone and joint areas will affect bone and cartilage metabolic activity via osteoclast maturation inhibition coupled with decreased cartilage degradation. This effect leads to decreased osteoarthritis progression and reduced pain, which is especially true if instituted early in osteoarthritis development.

An example of strontium carbonate and natural organic acid chemical reaction is:

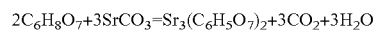

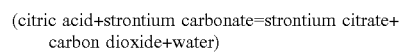

(citric acid+strontium carbonate=strontium citrate+ carbon dioxide+water)

The salts of strontium carbonate in the oral cavity produced by the example chemical reaction (strontium citrate, strontium ascorbate, strontium malate, or strontium folate) are suspended in close oral cavity proximity to the xylitol ingredient. Therefore, small bowel gastrointestinal lumen solubility and gut wall assimilation are improved because strontium citrate or malate is more soluble than insoluble strontium carbonate. The simultaneous chemical reactions also produce water as a by-product and stimulate parotid gland saliva flow, thus affording direct periodontal and tooth surface irrigation.

Table 1 illustrates exemplary absolute weight ranges in milligrams (mg), including preferred ranges and preferred amounts, for each ingredient comprised in the blend of ingredients for each rounded quarter to three-eighths teaspoon (¼-⅜ tsp) dose of the blend of ingredients. It shall be understood that absolute weight ranges and amounts discussed herein are in relation to one rounded ¼-⅜ tsp dose of the blend of ingredients. In an embodiment, each rounded ¼-⅜ tsp dose may be about 1.85-2.25 cubic centimeters.

TABLE 1

| Ingredient | Exemplary wt range | Preferred wt range | Preferred wt amount |
| --- | --- | --- | --- |
| Strontium carbonate | 500-1500 mg | 800-1200 mg | 1100 mg |
| Citric acid | 50-150 mg | 50-75 mg | 75 mg |
| Ascorbic acid | 50-150 mg | 50-75 mg | 75 mg |
| Malic acid | 50-150 mg | 50-75 mg | 75 mg |
| Folic acid | 0.5-2 mg | 0.75-1.5 mg | 1 mg |
| Vitamin d3 | 0.002-0.007 mg | 0.002-0.005 mg | 0.003 mg |
| Magnesium citrate | 50-100 mg | 50-75 mg | 50 mg |
| Stevia | 5-15 mg | 10-15 mg | 12 mg |
| Xylitol | 100-1000 mg | 500-1000 mg | 750 mg |
| Flavoring | 10-60 mg | 30-50 mg | 40 mg |

Referring to Table 1, in exemplary embodiments, the blend of ingredients comprises at least at least 500 mg of strontium carbonate to achieve the aforementioned advantages and effects. The element of strontium is not known to be toxic in this range to humans or other animals. Therefore, in other exemplary embodiments, the blend of ingredients may comprise 500-1500 mg of strontium carbonate. In preferred embodiments, the blend of ingredients may comprise 800-1200 mg of strontium carbonate, which provides approximately 480-720 mg of elemental strontium in a day.

In order to support the "in-vivo" chemical reaction in the oral cavity, in exemplary embodiments, the blend of ingredients comprises 50-150 mg of each of citric acid, ascorbic acid, and malic acid. In preferred embodiments, the blend of ingredients may comprise 50-75 mg of each of citric acid, ascorbic acid, and malic acid. Additionally, in exemplary embodiments, the blend of ingredients comprises 0.5-2 mg of folic acid. In preferred embodiments, the blend of ingredients may comprise 0.5-0.75 mg of folic acid.

As discussed above, intestinal absorption of the strontium salts is improved once in luminal contact with vitamin d and magnesium salts. Therefore, in exemplary embodiments, the blend of ingredients comprises 2-7 mcg of vitamin d3 and 50-100 mg of magnesium citrate. In preferred embodiments, the blend of ingredients may comprise 2-5 mcg of vitamin d3 and 50-75 mg of magnesium citrate.

In exemplary embodiments, a natural sweetener may be included in the blend of ingredients to enhance more pleasurable oral consumption and thus facilitate long-term use, compliance, effectiveness, and market durability of the present invention. In an exemplary embodiment, the sweetener may be a stevia glycoside present in a refined granular mode that has no bitter aftertaste, xylitol, or a combination of both. Accordingly, in exemplary embodiments, the blend of ingredients comprises 5-15 mg of stevia and 100-1000 mg of xylitol, or preferably 10-15 mg of stevia and 500-1000 mg of xylitol.

In exemplary embodiments, flavoring, coloring agents, and the like may be included in the blends of ingredients to further enhance more pleasurable oral consumption. Flavoring may be in the form of flavored powdered or granular extracts, volatile oils, or any commercially available flavoring. Examples of useful flavoring include, but are not limited to, pure anise extract, cherry extract, grape extract, chocolate extract, pure lemon extract, pure orange extract, strawberry extract, or pure vanilla extract; or volatile oils, such as walnut oil, cherry oil, cinnamon oil, clove oil, or peppermint oil. Accordingly, in exemplary embodiments, the blend of ingredients comprises 10-60 mg of sweetener and flavoring.

In preferred embodiments, the blend of ingredients may comprise 30-50 mg of flavoring.

In exemplary embodiments, the foregoing ingredients are combined in the specified amounts and mixed, using conventional methods such that the ingredients are evenly distributed, to form a blend of ingredients. The blend of ingredients may be delivered in any suitable format. In preferred embodiments, the blend of ingredients is formulated for oral delivery.

In an exemplary embodiment, the blend of ingredients may be contained in an acceptable carrier for oral consumption. For example, the carrier may be a liquid, gel, gelcap, capsule, powder, solid tablet (coated or non-coated), tea, oral spray, or the like. In preferred embodiments, the carrier may be an ingredient-enriched dissolvable tablet, an ingredient-enriched soft "gummy" tablet, an ingredient-enriched lozenge, a toothpaste, an oral spray, or a piece of sugarless chewing gum.

In another exemplary embodiment, the blend of ingredients may be in the form of a dry powder. In an exemplary embodiment, the dry powder blend of ingredients may be applied directly to the tooth surface using a tooth brush or with a piece of sugarless gum, for example. In a preferred embodiment, the dry powder blend of ingredients is mixed in the oral cavity with saliva or a small amount of fluid to facilitate formation of a slurry. For example, the blend of ingredients may be mixed with 2 ounces of water to form the slurry. The slurry is subsequently swished in the oral cavity, such as for thirty seconds, and swallowed.

The aforementioned advantages and effects may be achieved by using the formulations and methods of delivery described in the foregoing embodiments of the present invention. Preferably, the all-natural strontium-based blend of ingredients is simply delivered to the oral cavity where an "in-vivo" chemical reaction takes place resulting in direct tooth and dentin exposure to facilitate direct dental anti-caries and anti-sensitivity strontium benefits. The blend of ingredients is then swallowed to establish intestinal transit and absorption to obtain the targeted benefits of systemic absorption to bone and joint areas.

The foregoing embodiments of the present invention may offer a non-traditional and inexpensive way to help control the progression of human (and other land animal) osteoarthritis, osteoporosis, and tooth decay in both developing and industrialized countries without noted side effect. This is in distinction to other formulations that are not natural and are pharmaceutically created "ex-vivo" such as strontium ranelate or other nutraceutical compositions such as strontium carbonate or citrate that are currently marketed only for bone health and presented in capsulated form, thereby bypassing direct oral (dental) exposure.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:

1. A strontium-based composition for controlling progression of osteoarthritis, osteoporosis, and tooth decay, the composition comprising a blend of ingredients, wherein each rounded ¼-⅜ tsp of the blend of ingredients comprises:
500-1500 mg of strontium carbonate;
50-150 mg of citric acid;

50-150 mg of ascorbic acid;
50-150 mg of malic acid;
0.5-2 mg of folic acid;
2-7 mcg of vitamin d3;
50-100 mg of magnesium citrate;
105-1015 mg of natural sweetener; and
10-60 mg of flavoring.

2. The composition according to claim 1, wherein each rounded ¼-⅜ tsp of the blend of ingredients comprises:
800-1200 mg of strontium carbonate;
50-75 mg of citric acid;
50-75 mg of ascorbic acid;
50-75 mg of malic acid;
0.75-1.5 mg of folic acid;
2-5 mcg of vitamin d3;
50-75 mg of magnesium citrate;
510-1015 mg of natural sweetener; and
30-50 mg of flavoring.

3. The composition according to claim 2, wherein the 510-1015 mg of natural sweetener comprises 5-15 mg of stevia and 100-1000 mg of xylitol.

4. The composition according to claim 3, wherein the composition comprises one rounded ¼-⅜ tsp of the blend of ingredients mixed with 2 oz. of water.

5. The composition according to claim 1, wherein the natural sweetener is at least one of stevia and xylitol.

6. The composition according to claim 1, wherein the blend of ingredients comprises only natural compounds.

7. A strontium-based product for controlling progression of osteoarthritis, osteoporosis, and tooth decay, the product comprising:
a blend of ingredients comprising:
500-1500 mg of strontium carbonate;
50-150 mg of citric acid;
50-150 mg of ascorbic acid;
50-150 mg of malic acid;
0.5-2 mg of folic acid;
2-7 mcg of vitamin d3;
50-100 mg of magnesium citrate;
105-1015 mg of natural sweetener; and
10-60 mg of flavoring; and
a carrier combined with the blend of ingredients.

8. The product according to claim 7, wherein the carrier is an ingredient-enriched soft tablet.

9. The product according to claim 7, wherein the carrier is an ingredient-enriched dissolvable tablet.

10. The product according to claim 7, wherein the carrier is an ingredient-enriched lozenge.

11. The product according to claim 7, wherein the carrier is a toothpaste.

12. The product according to claim 7, wherein the carrier is a piece of chewing gum.

13. The product according to claim 7, wherein the carrier is an oral spray.

14. A method of delivering a strontium-based composition for controlling progression of osteoarthritis, osteoporosis, and tooth decay, the composition comprising one rounded ¼-⅜ tsp of a blend of ingredients in a dry powder form, the blend of ingredients comprising 500-1500 mg of strontium carbonate, 50-150 mg of citric acid, 50-150 mg of ascorbic acid, 50-150 mg of malic acid, 0.5-2 mg of folic acid, 2-7 mcg of vitamin d3, 50-100 mg of magnesium citrate, and 105-1015 mg of natural sweetener; and 10-60 mg of flavoring, the method comprising:
mixing the blend of ingredients with 2 oz. of water to form a slurry;
swishing the slurry in an oral cavity; and
swallowing the slurry after the swishing.

\* \* \* \* \*